United States Patent [19]
Bartlett

[11] Patent Number: 6,074,355
[45] Date of Patent: Jun. 13, 2000

[54] KNEE BRACE

[76] Inventor: Edwin Clary Bartlett, 609 Bremerton Dr., Greenville, N.C. 27858

[21] Appl. No.: 09/020,045

[22] Filed: Feb. 6, 1998

[51] Int. Cl.⁷ .................................................. A61F 5/00
[52] U.S. Cl. .............................................. 602/16; 602/26
[58] Field of Search ................................. 602/16, 23, 20, 602/26; 128/882, 892; 623/27, 57

[56] References Cited

U.S. PATENT DOCUMENTS

| | | |
|---|---|---|
| 4,271,831 | 6/1981 | Delbert . |
| 4,732,143 | 3/1988 | Kausek et al. . |
| 4,865,024 | 9/1989 | Hensley et al. . |
| 4,955,369 | 9/1990 | Bledsoe et al. . |
| 5,230,696 | 7/1993 | Silver et al. ............................ 602/16 |
| 5,288,287 | 2/1994 | Castillo et al. . |
| 5,472,412 | 12/1995 | Knoth . |

FOREIGN PATENT DOCUMENTS

| | | |
|---|---|---|
| 0413424A1 | 2/1991 | European Pat. Off. . |

OTHER PUBLICATIONS

PCT International Search Report, PCT/US99/02668, mailed Jun. 10, 1996.

*Primary Examiner*—Richard J. Apley
*Assistant Examiner*—Jayne Saydah
*Attorney, Agent, or Firm*—Alston & Bird LLP

[57] ABSTRACT

There is provided a testing device for determining the amount of tension in the quadriceps muscle for the anterior cruciate ligament to fail. There is also provided a knee brace having three point fixation and includes a pair of first arm members positioned on opposite sides of the knee joint. The lower leg brace member has a pair of second arm members oriented and positionable on opposite sides of the knee joint. The rigid thigh member and lower leg member are secured to the wearer's leg by means of a flexible strap extending around the back of the leg and adjustably attached thereto. The mating ends of the arms are connected by a pair of parallel spaced-apart face plates forming polycentric hinges which permit the mating ends of the arms to pivot about the connections. Various forms of extension cushions are provided to limit the proximity of the mating ends to one another to thereby limit the forward movement of the arms.

6 Claims, 4 Drawing Sheets

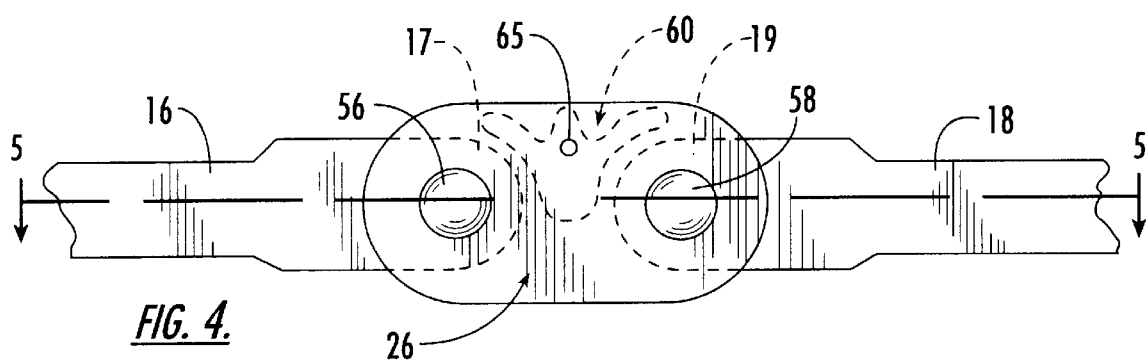
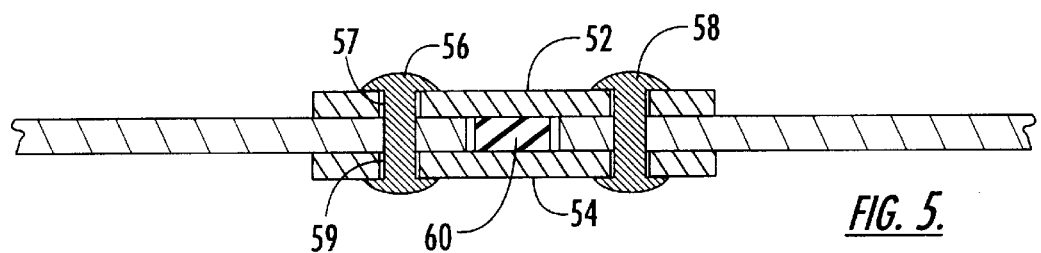
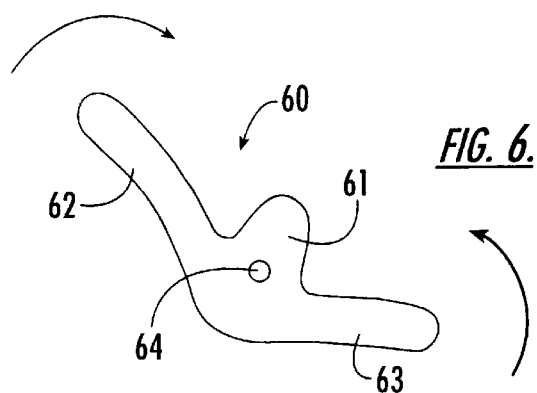
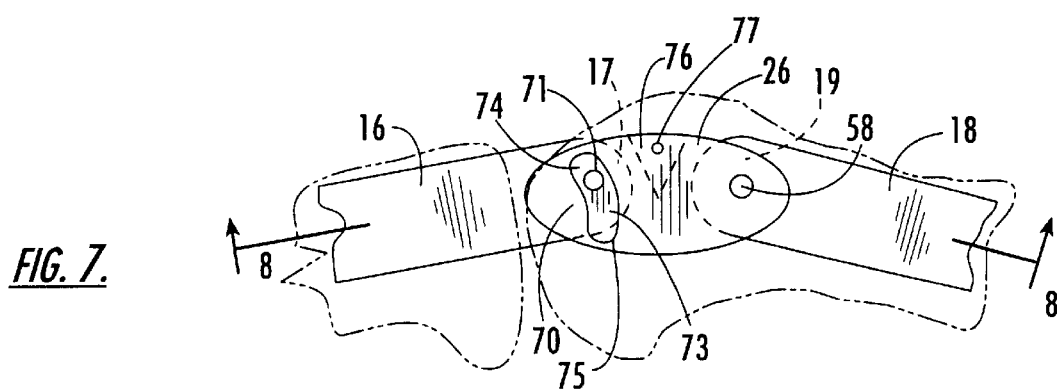

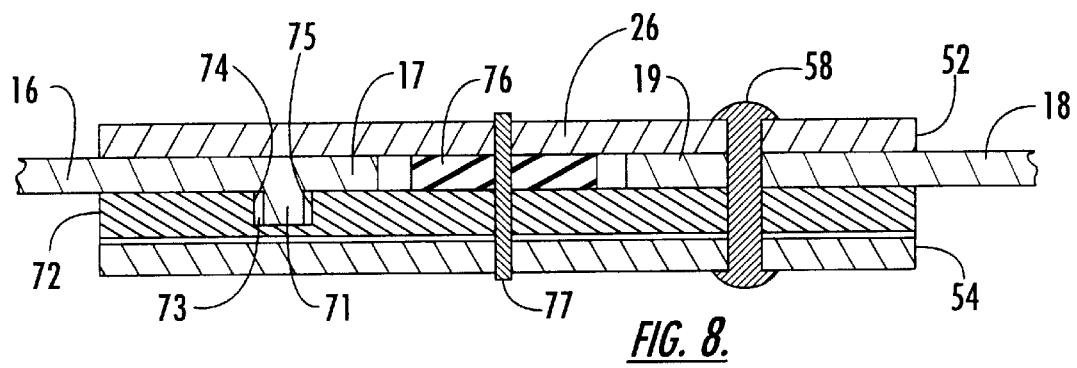
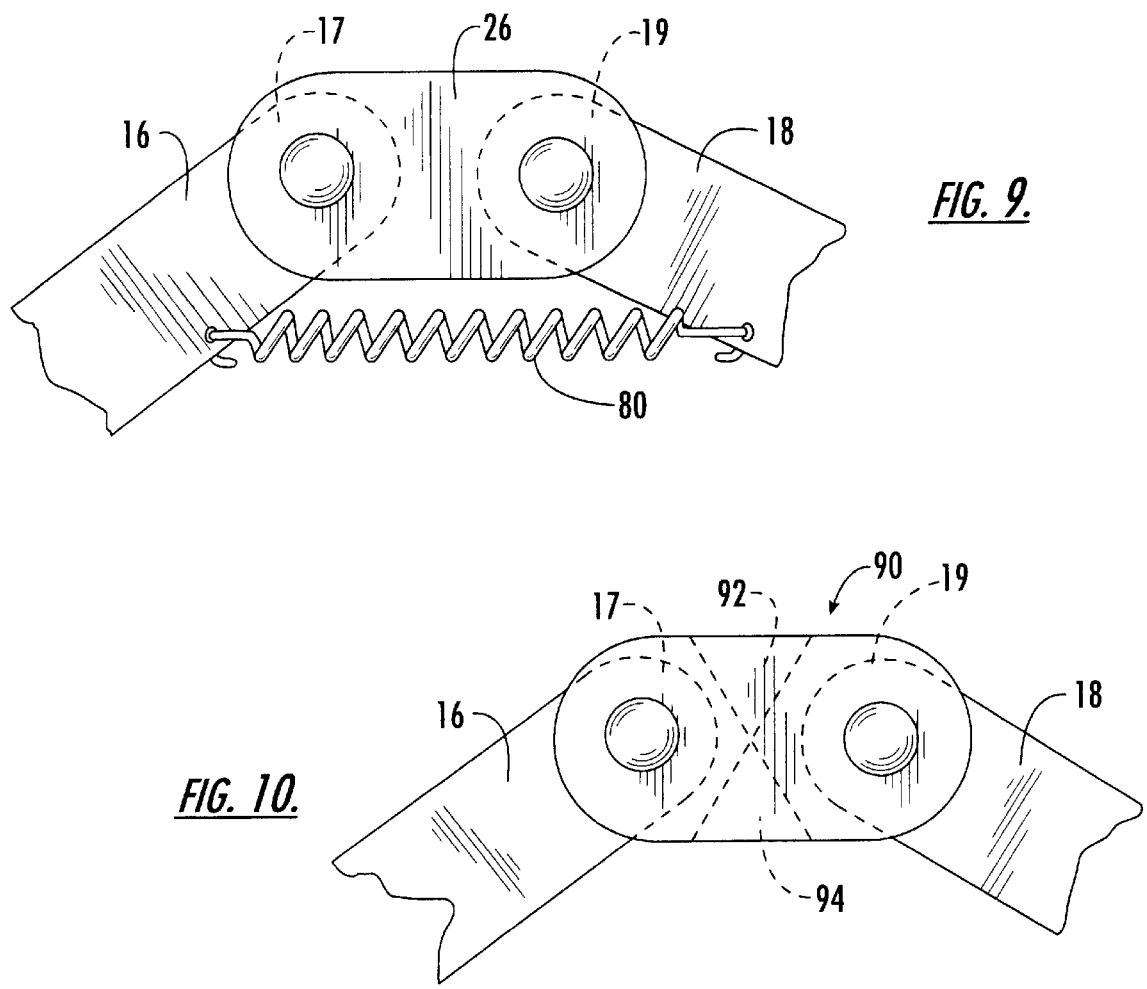

KNEE BRACE

BACKGROUND OF THE INVENTION

The present invention relates to knee braces. More particularly, the present invention relates to a knee brace having three point fixation with an extension cushion to relieve forces against the anterior cruciate ligament in response to extension of the leg.

As the leg extends toward its fully straightened position the anterior shifting force imposed by the quadriceps muscle on the tibia is counteracted by the anterior cruciate ligament to prevent the tibia from being anteriorly shifted away from its normal position relative to the femur. When the anterior cruciate ligament is damaged the quadriceps muscle causes an undesirable tibial shift. It is therefore desirable to counter the anterior force imposed by the quadriceps muscle by imposing a counteractive force on the tibia using a knee brace.

Not surprisingly, there have been numerous attempts to prevent and decrease damage to the anterior cruciate ligament. One such example is U.S. Pat. No. 4,955,369 to Bledsoe which discloses a dynamically shiftable knee brace used to counteract anterior tibial displacement caused during leg extension by the quadriceps muscle or when the anterior cruciate ligament is missing or damaged. The brace includes pairs of thigh and calf support members which extend along and are strapped to thigh and calf portions of the leg. The support member pairs are pivotally connected at their inner ends to one another by a pair of specially designed hinges positioned on opposite sides of the knee. As the leg is extended from a flexed position toward its fully straightened position the hinges cause a relative anterior-posterior shift between the support member pairs in a manner creating a shear force across the knee which is opposite that generated by the quadriceps muscle.

In another patent, U.S. Pat. No. 4,271,831 to Deibert, there is provided a knee brace which is hinged at the knee joint of the wearer and includes a hammock device for drawing the tibia forward into a desired position using a strap to encircle the tibia and secure the tibia in the desired position. This brace is particularly suitable for those with an injured posterior cruciate ligament.

When the ligaments around the knee have been damaged it is desirable to prevent the knee from hyperextending. One way to prevent hyperextension is to provide a mechanism to prevent the knee from entirely straightening out. In this regard, U.S. Pat. No. 4,732,143 to Kausek et al. discloses a knee brace having a selectable extension stop for a polycentric hinge which prevents the knee from straightening out. The hinge has a pair of rigid arms connected at spaced-apart pivotal connections between a pair of parallel face plates. Intermeshing gear teeth are provided on the mating ends of the arms causing simultaneous pivoting action of both arms about their pivotal connections with the plates. An extension stop of rigid material is provided to prevent hyperextension of the knee. The extension stop is a C-shaped plastic body which is attachable along one of the face plates. The extension stop includes a resilient clip for attaching the stop to one of the face plates and an extendable block at the opposing end positionable between the mating ends of the arms to limit the forward rotation of the arms. The difficulty with a knee brace of this type is that its use of a rigid extension stop does not allow for a soft cushioning of the knee as the leg reaches its desired extension.

U.S. Pat. No. 5,288,287 to Castillo et al. discloses another knee brace having thigh and calf frame members connected by a polycentric hinge. Attached to the inner surface of the lower frame member is a tibia pad which is used to provide a firm interface between the lower frame members and the portion of the knee joint adjacent the crest of the tibia. Means are provided to adjust the position of the tibia pad relative to the knee joint. This brace also includes a rigid extension stop.

The disadvantages of the prior art braces is the inability to dynamically deliver a post shear force countering displacement forces. There remains a need for a knee brace capable of providing a soft cushioning of the knee as the leg reaches its desired extension.

SUMMARY OF THE INVENTION

It is an object of the present invention to provide a knee brace having three point fixation with an extension cushion made to deliver a posterior shear force appropriate to the needs of the patient.

Another object of the present invention is to focus on the specific forces exerted by the quadriceps muscle during flexion and extension of the knee to delete unneeded components of knee braces thereby making the braces lighter and increasing performance.

Still another object of the present invention is to provide a testing device for determining the amount of tension in the quadriceps muscle for the anterior cruciate ligament to fail.

The knee brace of the present invention includes a thigh brace and lower leg brace members attached to the wearer's leg. The thigh brace member fits over the front of the leg and includes a pair of first arm members positioned on opposite sides of the knee joint. The lower leg brace member includes a pair of second arm members oriented and positionable on opposite sides of the knee joint.

The rigid thigh member and lower leg member are each secured to the wearer's leg by means of a flexible strap extending around the back of the leg and adjustably attached thereto with a VELCRO®-type fastener. Three point fixation is provided by a thigh member which encircles the back of the thigh along upper arm members and provides a posterior thigh force. The strapping system allows the wearer to control delivery of stabilizing forces by how tightly they strap on the brace.

The mating ends of each pair of arms are preferably joined by a polycentric hinge. The mating ends are pivotally secured to the face plates at spaced-apart pivotal connections which permit the mating ends of the arms to pivot about the connections. Lateral and medial condylar pads are mounted directly on the hinge plates and engage against opposite sides of the knee to cushion and control lateral knee instability.

The present invention provides various forms of extension cushions mounted to the polycentric hinge. These extension cushions are provided to limit the proximity of the mating ends to one another to limit the forward movement of the arms. It is important that the extension cushions allow the knee to slow down or be cushioned as the extension reaches its forwardmost point. In one preferred embodiment of the extension cushion there is provided an extension cushion with flexible wings that provide a spring action. In another embodiment there is provided an extension cushion of resilient material such as soft rubber that is of such hardness as to provide a posterior shear force as the leg reaches its desired extension. In still another embodiment a hydraulic reservoir is provided which allows the fluid to pass from one side of the hinge to the other as the leg is flexed. In still another embodiment a spring is connected between the legs.

BRIEF DESCRIPTION OF THE DRAWINGS

Other objects, features and advantages of the present invention will become apparent from the following detailed description taken in conjunction with the accompanying drawings in which:

FIG. 4 is a partial section view of the arms, polycentric hinge, and an extension cushion of the present invention;

FIG. 5 is a view of the polycentric hinge of FIG. 4 taken along line 5—5;

FIG. 6 shows an embodiment of the winged extension cushion of the present invention;

FIG. 7 show another form of polycentric hinge for use with the present invention having a dynamically shifting cam mechanism and an extension cushion;

FIG. 8 is a view of the polycentric hinge of FIG. 7 taken along line 8—8;

FIG. 9 shows an embodiment of a hinge extension cushion of the present invention in the form of a spring; and FIG. 10 shows another embodiment of a hinge extension cushion of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
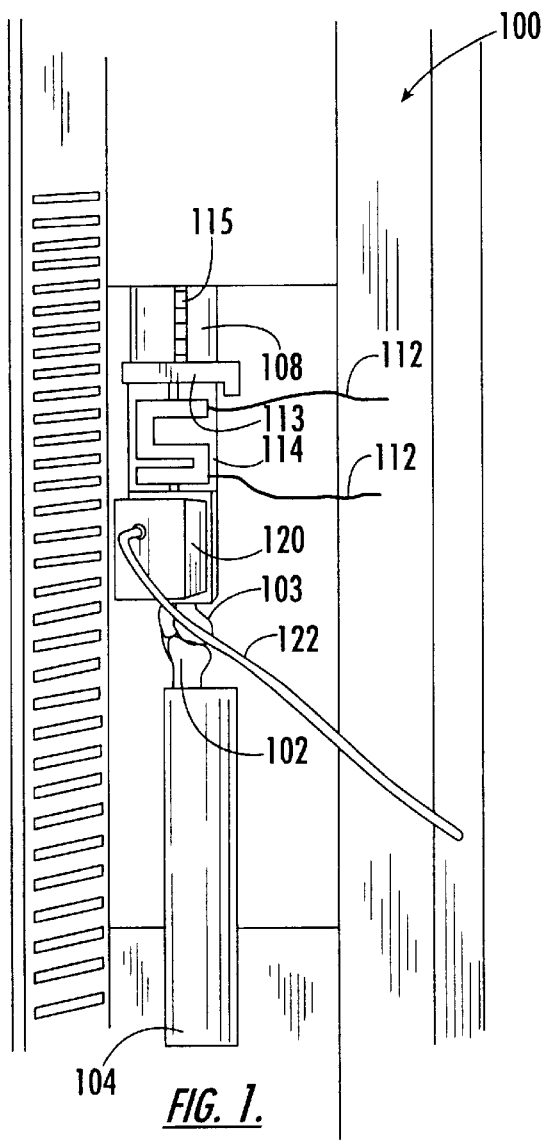
FIG. 1 illustrates the testing device used to determine the tension force delivered by the quadriceps muscle to the anterior cruciate ligament.

The ability to provide a knee brace to relieve forces against the anterior cruciate ligament is aided by using a biomechanical testing device, such as the one shown in FIG. 1, for the distribution of forces found in nature that create noncontact injuries in the knee. More specifically, the exertion of the forces of the quadriceps muscle as it acts on the knee often time can cause ligament injury and instability across the knee joint just by the amount of force created in the quadriceps.

Figure 1A:
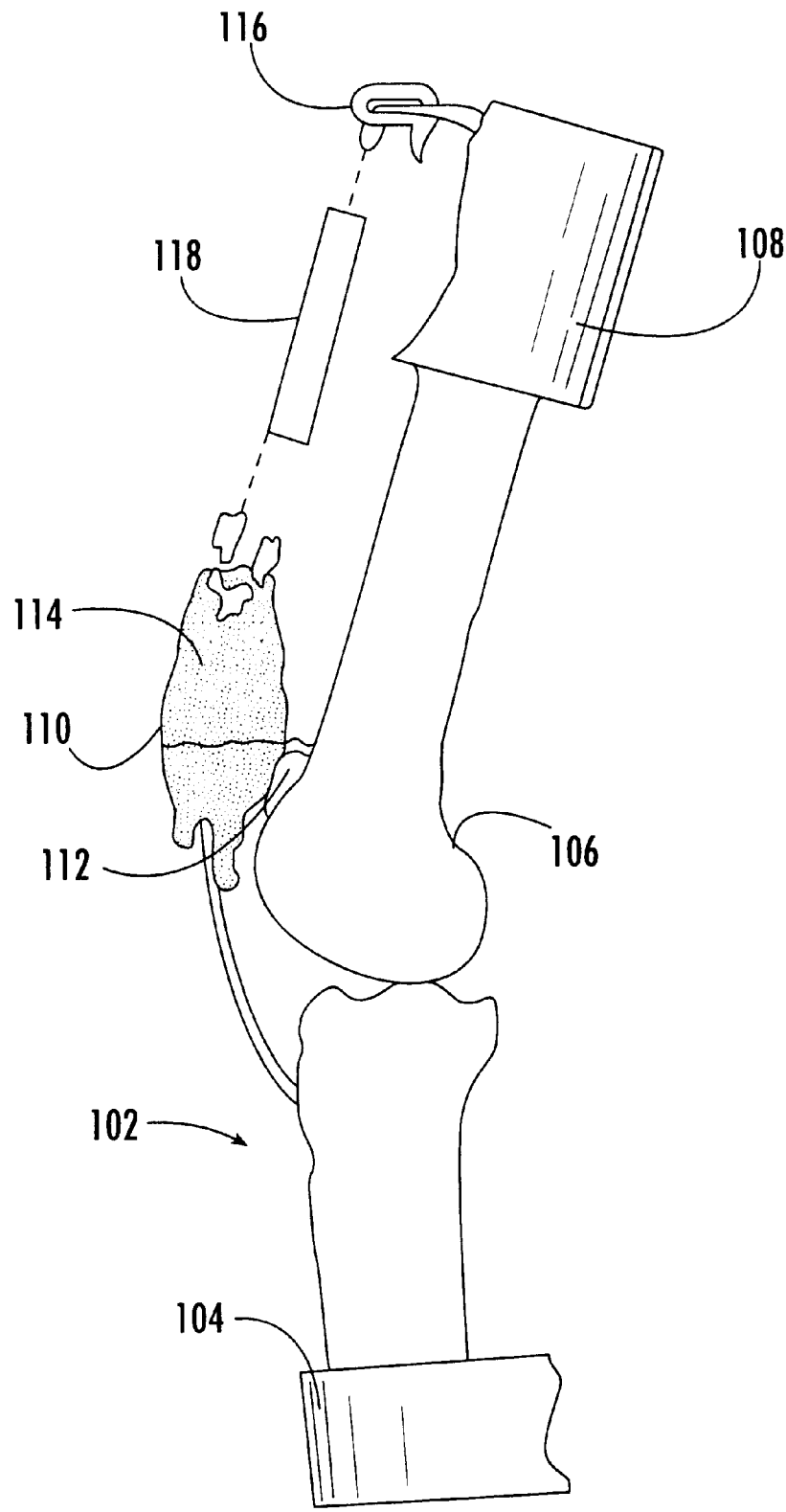

The testing device 100 provides a tethered quadriceps muscle in which forced bending of the knee markedly increases the tension in the quadriceps muscle to the failure level and can, by the directions of the forces, cause rupture of the anterior cruciate ligament. As shown in FIG. 1 and 1A, a cadaver leg with most of the tissue removed is placed in the testing device 100 with the tibia 102 potted in pipe 104 fastened to the bottom of the testing device. The femur is potted to upper pipe 108 mounted to the upper portion of the testing device 100. It has been found helpful in conducting the tests to provide a cryogenic clamp 120 slightly above the knee 103 connected to a gas supply via line 122. The cryogenic clamp 120 is fitted to the quadriceps tendon and freezes the tendon for the experiment. A load cell 114 having a first portion is attached to and above the cryogenic clamp. The tension exerted from the bending of the leg is determined from the current received from signal wires 112 running from the load cell 114 to a computer (not shown). Attached to a second portion of the load cell 114 is quadriceps pipe clamp mechanism 113 which is tethered to the upper potting pipe 108. The upper end of the tension testing device is attached to the frame of the tester through hinge attachment 115. The signals from the load cell are converted into data to show the shear force needed for failure of the anterior cruciate ligament.

The essence of the testing device is that the forces are tested at the point of range of motion in which the knee is most vulnerable. After the knee bends about 30°, there is a considerable amount of inherent geometric stability as well as accessory stabilizing structures that make it more difficult to injure the knee or isolate our any particular ligament for damage or destruction. The testing device focuses on the vulnerable range of motion of the knee from 0° to about 30°. The testing device is designed to exert massive forces in the quadriceps tendon with the knee at approximately 15° and observe the changes there as well as making measurements of the tension forces and applying them to a mathematical model.

As a result of tests conducted on knees in the testing device a knee brace was developed to incorporate static resistance to anterior tibial translation through a cushioned mechanism and translate this resistance to the thigh through a series of straps and securing devices. The results of which are described below.

Figure 2:
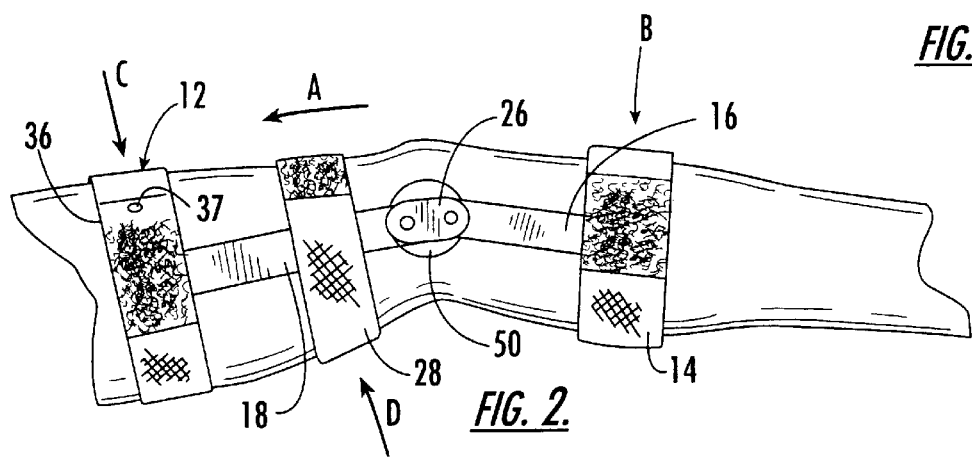
FIG. 2 illustrates the mechanical forces delivered to a leg during extension and contraction of a knee having a brace attached thereto.

As illustrated in FIG. 2, as the quadriceps muscles contract, shown by arrow A, forcing the knee into full extension (0°), the brace 10 creates a posterior tibial shear force, arrow B, at the tibial tubercle, which is controlled by the tightness of the tension control straps. These forces also result in an anterior thigh force, arrow C, though the rigid thigh brace member 12. A posterior thigh force, arrow D, results at thigh member 28. These forces are converted to energy to make the knee more stable.

Figure 3:
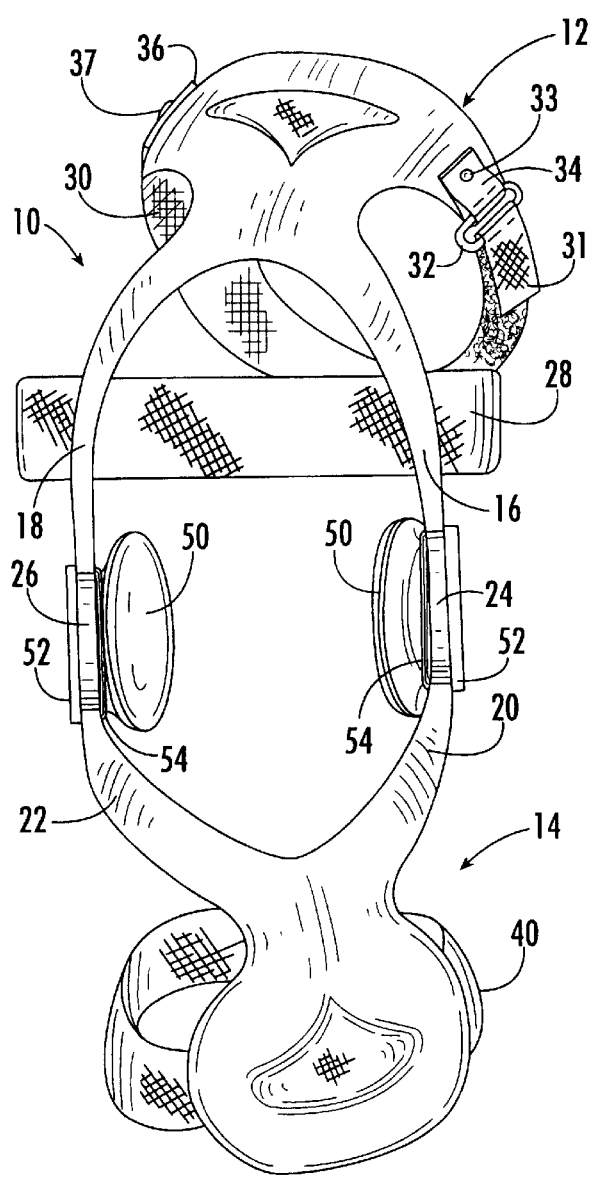
FIG. 3 is a perspective view of a knee brace for use with the present invention.

Referring now to FIG. 3, there is shown a knee brace 10 which utilizes the extension stop of this invention. The knee brace shown in FIG. 3 may be adapted for the right leg or the left leg and is by way of example only. It is understood that the invention may be used with various braces having a polycentric hinge. The knee brace 10 includes a rigid thigh brace member 12 attached to the wearer's upper leg and a rigid lower leg brace member 14 attached to the wearer's lower leg. The rigid thigh brace member 12 is shaped to fit over the front of the leg and includes a pair of first arm members 16, 18 positioned on opposite sides of the knee joint. The lower leg brace member 14 includes a pair of second arm members 20, 22 also oriented and positionable on opposite sides of the knee joint. In one embodiment of the invention, the upper thigh brace member 12 and lower leg brace member 14 are formed from a fiber reinforced composite material having sufficient rigidity to withstand impact forces encountered during physical sport endeavors yet be sufficiently light in weight so as not to impair the physical sport activity. However, other materials possessing sufficient strength and rigidity are contemplated.

The rigid thigh member 12 is secured to the wearer's leg by means of a flexible strap 30. Strap 30 extends around the back of the leg and is adjustably attached by passing one end 31 through a metal ring 32 secured by a plastic tab 34 and a rivet 33 to the rigid thigh member 12 and securing end 31 of strap 30 to another portion of strap 30 with a VELCRO®- type attachment. The opposing end 36 of strap 30 is permanently attached to the medial side edge of thigh member 12 by fastener 37. Lower leg brace member 14 is secured to the wearer's calf by flexible strap 40 wrapped around the back of the leg in the middle of the calf. The strap 40 is attached to lower leg member 14 in the same manner as the attachment of the upper strap.

A thigh member 28 of rigid material encircles the back of the thigh along upper arm members 16, 18. As noted in FIG. 2, rigid thigh member 28 serves to provide a posterior thigh force D.

Arm members 18 and 22 are joined together at their mating ends 17, 19 by a polycentric hinge 26. In a like manner arm members 16 and 20 are joined together at their mating ends by polycentric hinge 24. As shown in FIG. 3, lateral and medial condylar pads 50 are mounted to the interior of each hinge 24, 26 and engage against opposite sides of the knee to cushion and control lateral knee instability.

As shown more clearly in FIG. 4, rigid arm member 18 extends downwardly from the rigid brace member 12 and arm member 22 extends upwardly from the lower leg member 14. The arms 18 and 22 are connected at their mating ends 17, 19 by polycentric hinge 26. Although not shown in FIG. 4, upper arm 16 and lower arm 20 are provided on the medial (inner) side of the leg and are connected by hinge 24. These opposite pairs of arms prevent lateral (i.e., side-to-side) and rotational or twisting movement of the knee. The hinges enable pivot of the thigh brace portion relative to the lower leg portion along a substantially horizontal hinge axis between position of extension and flexion when attached to the wearer's leg.

Each of the hinges 24, 26 are formed by joining the mating ends of the arms between a pair of parallel spaced-apart face plates 52, 54. The mating ends are pivotally secured to the face plates at spaced-apart pivotal connections by means of rivets 56, 58 which extend through aligned apertures in the face plates and the mating ends (see FIG. 5). The rivets pass through brass bushings 57, 59, which permit the mating ends 17, 19 to pivot about the connections.

In one embodiment of the present invention an extension cushion 60 is disposed between the mating ends 17, 19 of arms 18, 22 and limiting the proximity of the mating ends to one another to thereby limit the forward movement of the arms. By the term extension cushion it is meant a device or element capable of providing a soft cushioning of the knee as the leg reaches its desired full extension, e.g., an element capable of delivering a posterior shear force appropriate to the needs of the patient. The extension cushion shown in FIGS. 4 and 6 is a spring action extension stop which has a body portion 61, and flexible wings 62, 63. As the knee extends the spring arms 62, 63 are rotated and compressed delivering a post shear force to the tibia. The extension cushion is mounted between the face plates 52, 54 of the polycentric hinge by inserting removable pin 65 through the face plates and the hole 64 in extension cushion 60. The extension cushion may be made of NITINOL™-type Nickel-titanium, rubber, plastic, steel or composite material. Several different cushions may be provided with each brace with the cushions varying in size and/or composition in order to vary the amount of cushioning appropriate for the needs of the patient.

In another embodiment of the present invention, shown in FIG. 7, the polycentric hinge is provided with a dynamically shifting cam mechanism 70. A cam follower 71 is mounted at the mating end 17 of arm 18. As shown in FIG. 8 there is provided a cam plate 72 having a cam 73 cut in the plate. Cam plate 72 fits between the face plate 54 and arm 18. The cam 73 is adapted to receive and mate with the cam follower 71. The dimensions of the cam 73 are such that upon engagement of the cam follower 71 with the cam 73, the cam is in slidable contact with the cam wall during movement of the cam follower 71. Thus, the cam 73 defines the path which the cam follower 71 must follow. The hinge face plates 52, 54 are fastened together by fasteners 58 such as rivets, screws or other means well known to those skilled in the art. Although the cam follower 71 may be an integral part of arm 18, it may also be a separate piece which is mounted to the mating end 17 of arm 18.

The cam edge surfaces define a path of rotational motion on arm 18 coinciding with a path of motion exhibited by flexion and extension of the knee. Each end of cam 73 forms a lobe 74, 75 which receives cam follower 71 at each end of the flexion and extension cycle and define stop points for the cam follower. The cam follower 71 rotates about the cam edge and permits a degree of motion between full flexion and full extension, as defined by the cam lobes 74, 75. Slidable contact between the cam follower 71 and the cam edge permits smooth articulation of the mechanical joint. There may also be provided a cap on cam follower 71 to cover the cam 73.

An extension cushion 76 of resilient material is provided at the terminus of the extension position to slow the final few degrees of extension. The extension cushion any be made of any material which is compressible to such a degree that the final 10° to 20° of extension is dramatically slowed. The extension cushion 76 is held in place by removable pin 77. The cam follower 71 is bounded on one side by face plate 54, on the other side by the arm 18, and on its sides by the cam edges.

In the embodiment shown in FIG. 9 the extension cushion is in the form of a variable tension spring 80. The tension spring extends between arm 18 and arm 22 and is connected to each arm so that as the knee is extended the spring is stretched providing a cushioning effect when full extension is reached. Alternatively, the spring 80 may be replaced by a rubber strap.

In yet another embodiment there is shown in FIG. 10 an extension cushion wherein the tensioning means is a hydraulic reservoir 90. The reservoir is positioned between face plates 52, 54 and between the mating ends 17, 19 of arms 18, 22. The reservoir is formed of a bladder of compressible fluid. As the knee is extended fluid is forced from the bladder outer chamber 92 through a channel to the inner chamber 94. The hydraulic system built into the extension cushion delivers an external resistance, i.e, posterior shear force.

The present invention provides a means for having a single hinge brace design that can be used for a variety of injuries.

The brace design of the present invention has been proven effective by clinical and biomechanical research. The brace is designed to utilize the natural hydraulics of the thigh muscles to clamp on and control effective brace movements. The brace offers more resistance when the quadriceps are contracted to produce a stiffer hydraulic system. The brace offers less resistance when the muscles are relaxed.

The knee brace further facilitates prospect training of the knee by allowing the wearer to control eccentric contracture and reversal of movements by landing on the bent knee.

One of the principal benefits of the extension stop of this invention is that because it is removable, the user can select an extension cushion having any of several different size extension blocks to limit both the extension of the arms and the speed at which the knee reaches full extension to any predetermined amount.

The extension cushions are useful in any type of polycentric hinge wherein it is desired to limit the extension of the arms connected by the hinge. The extension stop would be useful in an elbow brace and in any other type of brace to permit limited pivotal movement. There are no special tools required to position the extension cushions nor any straps to adjust and readjust. The extension cushions provide a precise, strong and reliable means for controlling the movement of the polycentric hinge.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A knee brace comprising:

a rigid thigh brace member adapted to be attached to the wearer's upper leg that includes a pair of first arms each having a mating end;

a lower leg brace member adapted to be attached to the wearer's lower leg that includes a pair of second arms each having a mating end;

a pair of hinges adapted to be disposed laterally on opposite sides of the knee when the thigh brace member and the lower leg brace member are attached to the wearer's leg, each hinge being operably connected between one of the first arms and one of the second arms to form a polycentric binge comprising a pair of parallel spaced-apart face plates wherein the arms are pivotally secured at the mating ends thereof between the face plates at spaced-apart pivotal connections, the hinges enabling pivoting of the thigh brace member relative to the lower leg brace member between a position of knee extension and knee flexion when attached to the wearer's leg each hinge further including an extension cushion configured to be resiliently pliant for cushioning and gradually limiting the forward pivotal movement of the first and second arms to a position of knee extension, the knee brace further adapted to concurrently deliver a posterior shear force to the tibia as the first and second arms move to a position of knee extension.

2. A knee brace according to claim 1 wherein said extension cushion comprises a spring action extension stop having a body portion and flexible elongate wings and being positioned between said mating ends of said first arm and said second arm, the wings being operably connected to the body portion and capable of engaging the mating ends of the first arm and the second arm such that the flexibility of the wings with respect to the body portion causes the extension cushion to be resiliently pliant ad thereby cushioning and gradually limiting the forward pivotal movement of the first and second arms to a position of knee extension.

3. A knee brace according to claim 2 wherein said extension cushion is made from a member of the group consisting of a type nickel-titanium alloy, rubber, plastic, steel and composite material.

4. A knee brace according to claim 1 wherein said extension cushion is a resiliently pliant material.

5. A knee brace according to claim 1 further comprising means for removably attaching said extension cushion to said hinge.

6. A knee brace according to claim 1 wherein the extension cushion is comprised of a shape memory material.

* * * * *

UNITED STATES PATENT AND TRADEMARK OFFICE
CERTIFICATE OF CORRECTION

PATENT NO. : 6,074,355
DATED : June 13, 2000
INVENTOR(S) : Bartlett

It is certified that error appears in the above-identified patent and that said Letters Patent is hereby corrected as shown below:

Column 7, line 38, "binge" should read --hinge--.

Column 8, line 7, after "leg" insert a comma (,); line 23, "ad" should read --and--; line 28, cancel "type".

Signed and Sealed this

Twenty-fourth Day of April, 2001

Attest:

NICHOLAS P. GODICI

*Attesting Officer*    *Acting Director of the United States Patent and Trademark Office*